(12) United States Patent
Lockwood et al.

(10) Patent No.: US 6,986,279 B2
(45) Date of Patent: Jan. 17, 2006

(54) METHOD AND APPARATUS FOR DETERMINING LIQUID ABSORPTION OF AGGREGATE

(75) Inventors: Mark D. Lockwood, Dubuque, IA (US); Steven C. Peake, Dubuque, IA (US)

(73) Assignee: Barnstead Thermolyne Corporation, Dubuque, IA (US)

(*) Notice: Subject to any disclaimer, the term of this patent is extended or adjusted under 35 U.S.C. 154(b) by 93 days.

(21) Appl. No.: 10/667,172

(22) Filed: Sep. 19, 2003

(65) Prior Publication Data

US 2004/0057335 A1 Mar. 25, 2004

Related U.S. Application Data

(63) Continuation-in-part of application No. 10/294,856, filed on Nov. 14, 2002, now abandoned, which is a continuation of application No. 09/643,329, filed on Aug. 22, 2000, now Pat. No. 6,486,475.

(51) Int. Cl.
G01N 5/02 (2006.01)
G01N 25/56 (2006.01)

(52) U.S. Cl. .................... 73/73; 73/866; 73/61.41; 366/139

(58) Field of Classification Search .................... 73/73, 73/61.41, 866; 366/139
See application file for complete search history.

(56) References Cited

U.S. PATENT DOCUMENTS

| | | | |
|---|---|---|---|
| 4,266,878 A | 5/1981 | Auer | |
| 4,871,917 A | 10/1989 | O'Farrell et al. | |
| 5,017,787 A | 5/1991 | Sato et al. | |
| 5,087,817 A | 2/1992 | Chiba et al. | |
| 5,220,168 A | 6/1993 | Adamski et al. | |
| 5,357,441 A | 10/1994 | Petty et al. | |
| 5,396,790 A | * 3/1995 | Koelliker et al. | .......... 73/61.72 |
| 5,590,976 A | 1/1997 | Kilheffer et al. | |
| 5,605,841 A | 2/1997 | Johnsen | |
| 5,755,041 A | 5/1998 | Horwitz | |
| 5,792,430 A | * 8/1998 | Hamper | ...................... 422/131 |
| 5,801,337 A | 9/1998 | Peake | |
| 5,870,926 A | 2/1999 | Saito et al. | |
| 5,908,240 A | 6/1999 | Hood | |
| 6,486,475 B1 | 11/2002 | Earle et al. | |
| 6,626,635 B1 * | 9/2003 | Prowse et al. | .................. 415/1 |

OTHER PUBLICATIONS

Marcel Dekker, Inc., *A Review On Absorption Of Asphalt Into Porous Aggregates*, Fuel Science And Technology Int'l., 11(5&6), 611-637 (1993).

(Continued)

*Primary Examiner*—Thomas P. Noland
*Assistant Examiner*—André K. Jackson
(74) *Attorney, Agent, or Firm*—Wood, Herron & Evans, L.L.P

(57) ABSTRACT

A method of determining liquid absorption of an aggregate comprises providing a shaker apparatus, a vacuum source and a container; placing a sample of the aggregate in the container; adding liquid to the container sufficient to reach a calibration mark on the container; weighing the sample and liquid; mounting the container to the shaker apparatus; connecting the vacuum source to the container; agitating the sample and liquid with the shaker apparatus; applying a vacuum to the sample and liquid with the vacuum source; after the agitation and vacuum steps, adding liquid to the container sufficient to again reach the calibration mark on the container; again weighing the sample and liquid; and subtracting the initial weight of the sample and liquid from the final weight of the sample and liquid in order to determine the liquid absorption of the aggregate.

12 Claims, 5 Drawing Sheets

OTHER PUBLICATIONS

Prithvi S. Kandhal, Rajib B. Mallick, Mike Huner, *Measuring Bulk-Specific Gravity Of Fine Aggregates*, Committee on Characteristics of Nonbituminous Components of Bituminous Paving Mixtures, Transportation Research Record, Paper No. 00-1230.

Barnstead International Product Center, *Vortex Maxi Mix® III Product Description/Operation*, www.barnsteadthermolyne.com/productline4, Jan. 27, 2003.

Instrutek, *Web-Shop Catalog*, www.instrutek.no/main.asp, Jan. 28, 2003.

* cited by examiner

METHOD AND APPARATUS FOR DETERMINING LIQUID ABSORPTION OF AGGREGATE

RELATED APPLICATIONS

Continuation-in-part of prior application Ser. No. 10/294,856, filed on Nov. 14, 2002 now abandoned, which is a continuation of Ser. No. 09/643,329 filed Aug. 22, 2000, now U.S. Pat. No. 6,486,475 issued Nov. 26, 2002

FIELD OF THE INVENTION

This invention relates generally to paving material, and more particularly to a method and apparatus for determining liquid absorption of aggregate. Specifically this invention is for determining the saturated, surface-dry state of aggregate and for determining the amount of water and hence binder absorbed by an aggregate in order to determine the proper amount of binder to be added to a given amount of aggregate to produce paving material or other construction materials of acceptable mechanical qualities.

BACKGROUND OF THE INVENTION

To design an asphalt paving mix, the proper amount of asphalt binder must be added to a given amount of aggregate material to maintain the right matrix of aggregate and binder in order to produce a paving material which will yield a strong and durable road. If there is too much binder in the mix, the road will be soft and rutting will occur. If there is not enough binder in the mix, the road will be brittle and will crumble or break apart.

Aggregates used in the preparation of asphalt for road construction are tested to determine the amount of asphalt binder that will be absorbed internally into the aggregate when a batch is prepared. When binder is absorbed internally into the porous aggregate, that absorbed binder does not contribute to the effective volume of the asphalt mix. In order to account for this, additional binder must be added, which essentially disappears in the mix. The measurement of the binder absorbed by the aggregate which does not contribute to the volume of the asphalt mix is the percent absorption, by weight, of water absorbed into the aggregate to the weight of the aggregate itself ("PA").

The procedure for testing aggregate for PA is as follows. A sample of the dry aggregate is prepared to a condition where the internal voids are saturated with water, and the surface of the aggregate is dry. This condition is known as the saturated surface dry ("SSD") state. The SSD sample is then weighed. The sample is then dried completely in an oven, and weighed again (dry). The difference between the SSD and dry weights, divided by the dry weight, and multiplied by 100, yields the PA.

The current method for determining whether aggregate is at SSD is what is known as the "slump" test. In this test, a sample of aggregate is prepared with excess water so that it is wetter than the SSD state. The aggregate is placed into a metal cone, the metal cone is placed atop a non-absorbent surface of a table or bench and the aggregate is tamped down into the cone, through an opening in the tip of the cone, with a metal tamper. With aggregate pieces having water on the surface, i.e. with the aggregate sample being wetter than the SSD state, the cone of aggregate will remain standing when the metal cone is removed. The water between the particles of aggregate holds the aggregate together, due to surface tension. The SSD point is reached when there is a "slight slump" of the aggregate when the metal cone is removed. Once the aggregate sample has been initially prepared to wetter than the SSD state the aggregate is progressively agitated and subjected to warm air flowing over it, repacked into the metal cone and the metal cone removed, until this slight slump occurs. A 500 gram sample is then taken from the SSD aggregate and weighed. The 500 gram sample is then completely dried in an oven and is weighed again. The PA is then computed from the two weights.

There are a number of problems with the slump test. First, the test is subjective. The definition of a "slight slump" will vary from technician testing the aggregate to the next. In addition, while the slump test works fairly well with natural sand, for which the test was originally developed, the test does not work as well for jagged material such as crushed granite and limestone. The crushed materials have a higher angularity (jaggedness) and a higher content of fine material, which packs better in the cone, holding the packed material together better. This requires the material to dry more before exhibiting a "slight slump", making for an artificially dryer SSD point. On the other hand, a method which could actually measure the presence or absence of water on the surface of the aggregate would give a much more accurate measurement of whether the aggregate was in the SSD state or not and hence produce a much more accurate PA measurement.

Second, when the sample is at a temperature above room ambient, it will continue to lose water weight by evaporation as long as the sample remains on the table or bench. This produces an artificially low PA. Also, the time between reaching SSD and weighing the sample will not be consistent from batch to batch and technician to technician. If the sample could maintain its SSD condition/moisture content from the time that that condition is reached until the sample is weighed then the measurement would be more accurate and repeatable from batch to batch and technician to technician.

Third, as the sample is agitated and dried, the sample will begin to generate dust, which leaves the sample, and thus alters the aggregate constitution. Dust can also adversely effect mechanical parts such as bearings, motors, couplings etc. of the equipment used in the SSD/PA testing, thus contributing to premature failure of same. The dust is also a nuisance to the technicians operating the equipment. It would be desirable to somehow contain the dust generated by the sample during the SSD/PA determination.

Knowing the liquid absorption of a material is valuable for a variety of reasons. First, the liquid absorption relates to the optimum amount of time the material should be processed in the preparation of asphalt mixes and concrete mixes. Second, from the liquid absorption one can calculate the film coefficient, which relates to the $V_{ssd}$, one of the parameters disclosed in the assignee's own U.S. Pat. No. 6,486,475, hereby incorporated by reference herein, which determines the SSD of the material.

Bulk specific gravity of an aggregate is defined as the weight of dry aggregate to the weight of weight having a volume equal to that of the aggregate including both its permeable and impermeable voids. Apparent specific gravity is defined as the ratio of dry aggregate to the weight of water having a volume equal to the solid volume of the aggregate excluding its permeable voids. One current method of determining the apparent specific gravity of a material sample involves soaking the material with water while manually hand agitating the material to remove air from the sample allowing water to displace the trapped air. Another current method of determining apparent specific gravity combines the step of pulling a partial vacuum on the vessel containing the specimen under test with manual hand agitation. Yet another current method has the technician pulling a vacuum on a pouch containing the sample to determine the apparent specific gravity, then puncturing the pouch under water to allow water into the sample to determine the liquid absorption. These methods are time consuming and prone to variation from one technician to the next.

SUMMARY OF THE INVENTION

The present invention solves the noted problems of the slump test, while providing for the liquid absorbing characteristics of aggregate to be determined. The invention is both method and apparatus for determining liquid absorption of aggregate, for determining the SSD state of an aggregate, and for determining the PA of an aggregate.

The method of determining SSD condition and related liquid absorption of an aggregate comprises providing a sample of the aggregate, adding liquid to the sample, subjecting the sample to a light source signal, monitoring a light reflected signal reflected from the sample and controlling either addition of liquid to the sample or removal of liquid from the sample as a function of the light reflected signal. Preferably the controlling step is controlling addition of liquid to the sample.

The liquid is preferably water. The light source signal is preferably an infrared source signal and the light reflected signal is preferably an infrared reflected signal.

The method further comprises agitating the sample. One manner of agitation comprises moving the sample in an orbital motion. Another manner of agitation comprises moving the sample in a wobbling motion. A third manner of agitation comprises stirring the sample. Preferably the agitating step comprises a combination of the three, namely moving the sample in an orbital motion, moving the sample in a wobbling motion and stirring the sample.

Preferably liquid is added to the sample only until the reflected light signal reaches a predetermined value indicative of the sample being at the SSD state. The predetermined value of the reflected light signal is determined by averaging the reflected light signal reflected from the dry sample with the reflected light signal reflected from the sample when wetter than the SSD state. The reflected light signal reflected from the dry sample, which can vary from aggregate to aggregate, is measured with the apparatus of the present invention and the value of the reflected light signal reflected from the sample wetter than SSD is approximately a constant 0.08 Volts for all aggregate.

Weighing the sample in the dry state and in the SSD state enables the technician to additionally determine the PA of the aggregate.

The method may further comprise heating the sample to remove liquid from the sample, with the controlling step controlling removal of liquid from the sample as a function of the reflected light signal by controlling the heating of the sample.

The apparatus of the present invention comprises a support for supporting a sample of the aggregate, a liquid source for adding liquid to the sample, a light source which subjects the sample to a light source signal, a light sensor which senses a reflected light signal reflected from the sample and a processor/controller which controls either addition of liquid from the liquid source to the sample or removal of liquid from the sample as a function of the reflected light signal. Preferably the processor/controller controls addition of liquid from the liquid source to the sample.

The liquid source is preferably a water source, the light source is preferably an infrared source and the light sensor is preferably an infrared detector.

The apparatus further preferably includes an agitator for agitating the sample. The agitator may be a turntable which moves the sample in an orbital motion, a turntable which moves the sample in a wobbling motion or a stirrer which stirs the sample. Preferably the agitator is a combination of all three, namely a turntable which moves the sample in an orbital motion and in a wobbling motion and a stirrer which stirs the sample.

The support is preferably a bowl which contains the sample. The bowl preferably includes an island in the center thereof to direct the sample radially outwardly. The bowl preferably concludes a lid thereon. The lid preferably includes a dome offset from the center of the lid. The light source and light sensor are preferably positioned such that the light source signal and light reflected signal pass through the dome normal to a surface of the dome. The light source is preferably an infrared source and the light sensor is preferably an infrared detector. The apparatus preferably includes a cabinet containing the support, the liquid source, the light source and the light sensor. The cabinet preferably includes a door providing access to an interior thereof. A bracket is preferably mounted to an underside of the door, and the light source and light sensor are preferably mounted to this bracket.

The processor/controller preferably processes the reflected light signal as a function of time and controls addition of liquid to the sample such that liquid is added to the sample only until the reflected light signal reaches a predetermined value indicative of the sample being at the SSD state. The reflected light signal reflected from the dry sample, which can vary from aggregate to aggregate, is measured with the apparatus of the present invention and the value of the reflected light signal reflected from the sample wetter than SSD is approximately a constant 0.08 Volts for all aggregate.

The apparatus may further preferably include a weight indicating device for weighing the sample in the dry state and in the SSD state to thereby additionally determine the PA of the aggregate.

The apparatus may further include a heater for removing liquid from the sample, in which case the processor/controller controls removal of liquid from the sample as a function of the reflected light signal by controlling the heater.

The present invention thus avoids the subjectivity of the slump test, replacing it with a much more scientific empirical test which actually measures the presence or absence of water on the surface of the aggregate. The present invention also avoids the problem of the slump test wherein continual water evaporation, after reaching SSD, produces an artificially low PA, since the moistened aggregate is maintained in a bowl sealed with a lid thereby preventing moisture escape. Further, the bowl with lid sealed thereon eliminates the generation of dust as the initially dry sample is begun to be agitated during initial addition of water to the sample.

In another aspect, the invention is a method of determining liquid absorption of an aggregate, comprising providing a shaker apparatus, a vacuum source and a container; placing a sample of the aggregate in the container; adding liquid to the container sufficient to reach a calibration mark on the container; weighing the sample and liquid; mounting the container to the shaker apparatus; connecting the vacuum source to the container; agitating the sample and liquid with the shaker apparatus; applying a vacuum to the sample and liquid with the vacuum source; after the agitation and vacuum steps, adding liquid to the container sufficient to again reach the calibration mark on the container; again weighing the sample and liquid; and subtracting the initial weight of the sample and liquid from the final weight of the sample and liquid in order to determine the liquid absorption of the aggregate.

The method can further comprise the steps of dividing the difference between the initial and final weights of the sample and liquid by the dry weight of the sample and liquid; and multiplying the quotient by a constant and by 100 to determine the percent liquid absorption of the aggregate. The constant is preferably about 0.5.

adding the dry sample weight to the weight of the container, sample and liquid with the liquid at the calibration mark on the container;

subtracting from that sum the final weight; and dividing that difference into the dry sample weight to determine the apparent specific gravity of the aggregate.

The agitation and vacuum steps can be performed simultaneously or sequentially. Preferably the agitation step is performed first and the vacuum step is performed second. Preferably a series of agitation steps are alternated with a series of vacuum steps. Preferably the agitation step is performed for about 5 minutes and then the vacuum step is performed for 5 about minutes. Preferably the vacuum step preferably applies a vacuum of about 22 inches of Hg. Preferably the vacuum step applies an initial vacuum of about 22 inches of Hg and a final vacuum of about 28 inches of Hg. Preferably agitation is performed for about 3 minutes, agitation and about 22 inches Hg vacuum is performed for about 3 minutes and agitation and about 28 inches Hg vacuum is performed for about 5 minutes.

In yet another aspect, apparatus for determining liquid absorption of an aggregate comprising a shaker apparatus for supporting and agitating a container containing a sample of the aggregate and liquid; a vacuum source for applying a vacuum to the sample and liquid; and a processor/controller operably associated with the shaker apparatus and vacuum source which controls operation of the shaker apparatus and vacuum source in response to inputs received from an operator of the apparatus.

The processor/controller preferably controls the vibration frequency, amplitude and duration of said shaker apparatus. The processor/controller preferably also controls the vacuum pressure and duration of said vacuum source. The apparatus can further comprising a weighing device; the processor/controller operably associated with the weighing device; the processor/controller operable to cause the weighing device to weigh the sample and liquid before and after operation of the shaker apparatus and vacuum source, to compute a percent liquid absorption of the sample from the weights of the weighing device and to display the percent liquid absorption of the sample.

These and other advantages of the present invention will become more readily apparent during the following detailed description taken in conjunction with the drawings herein, in which:

BRIEF DESCRIPTION OF THE DRAWINGS OF THE INVENTION

DETAILED DESCRIPTION OF THE INVENTION

Figure 1:
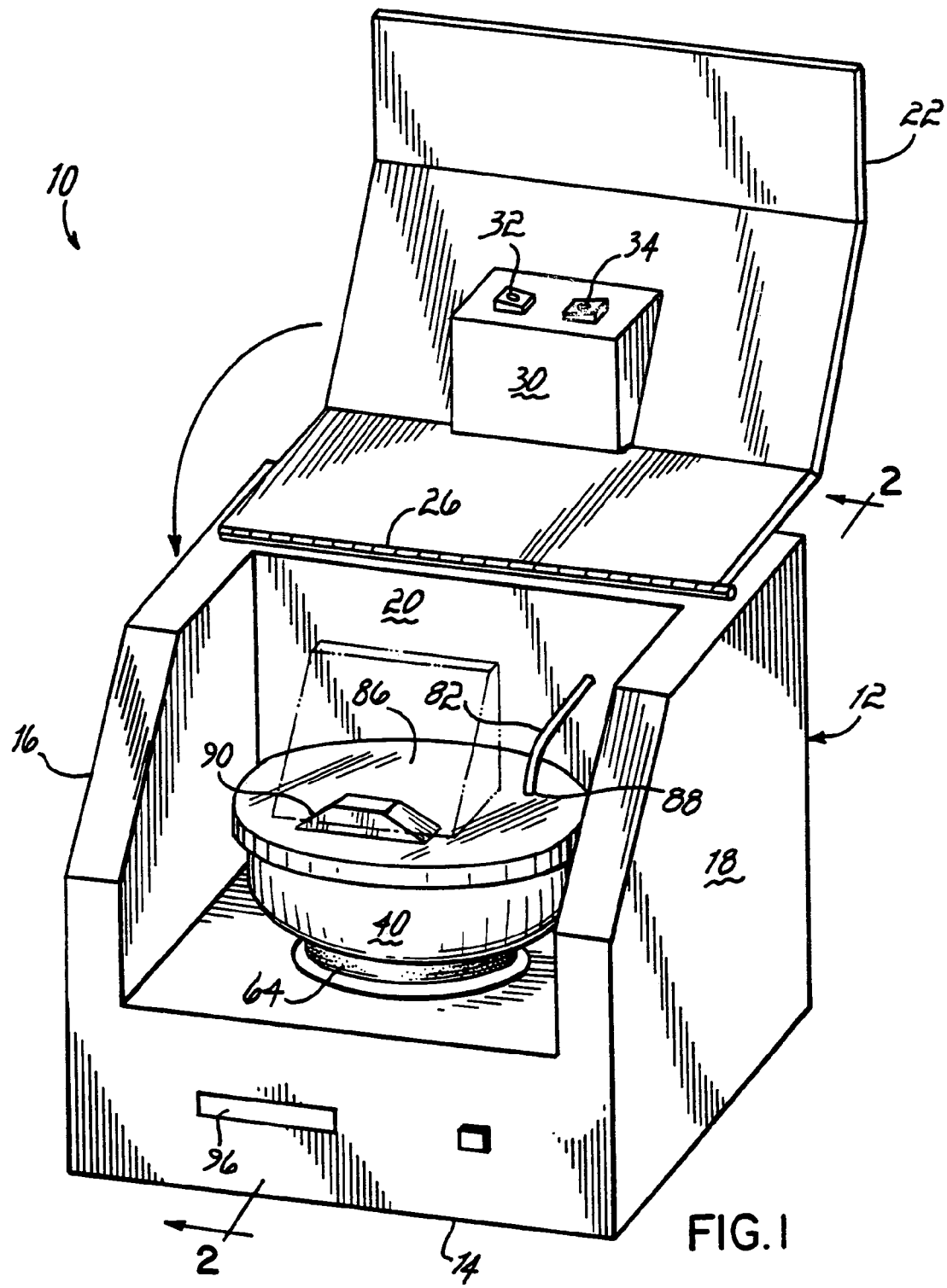
FIG. 1 is a perspective view of the apparatus of the present invention.

Referring first to FIG. 1, there is illustrated apparatus 10 embodying the principles of the present invention for determining liquid absorption of aggregate, for determining the SSD state of an aggregate and for determining the PA of an aggregate.

The apparatus 10 comprises a cabinet 12 having a base 14, a pair of opposed side walls 16, 18 and a back wall 20. An openable and closeable door 22 is pivoted to a partial top wall 24 via hinge 26 and forms the remainder of the top and front of the cabinet 12. Mounted to the underneath side of the door 22 is a bracket 30 to which are mounted an infrared source 32 and an infrared detector 34, the operation of which will be described below.

Figure 2:
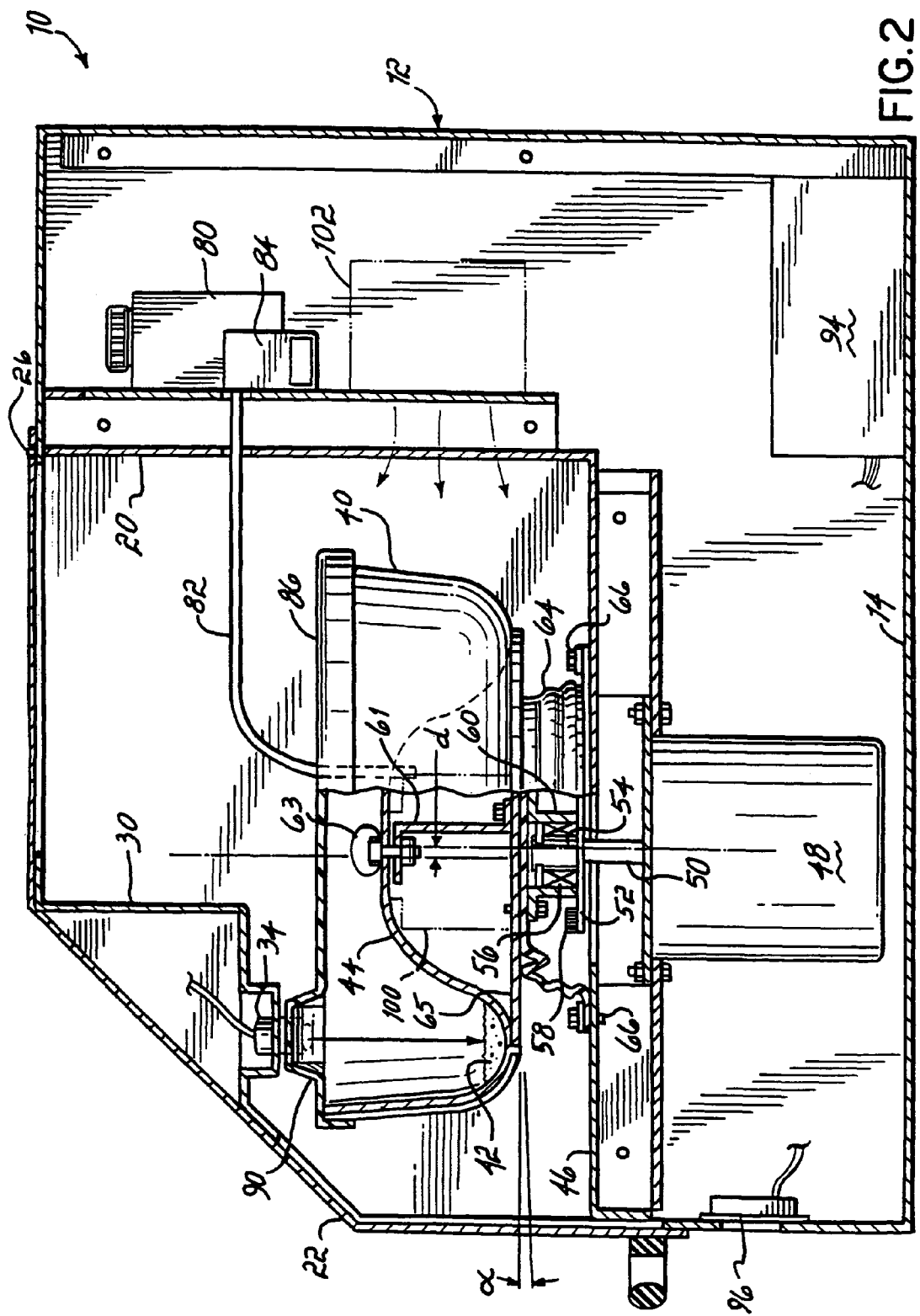
FIG. 2 is a view taken along line 2—2 of FIG. 1.
Figure 3:
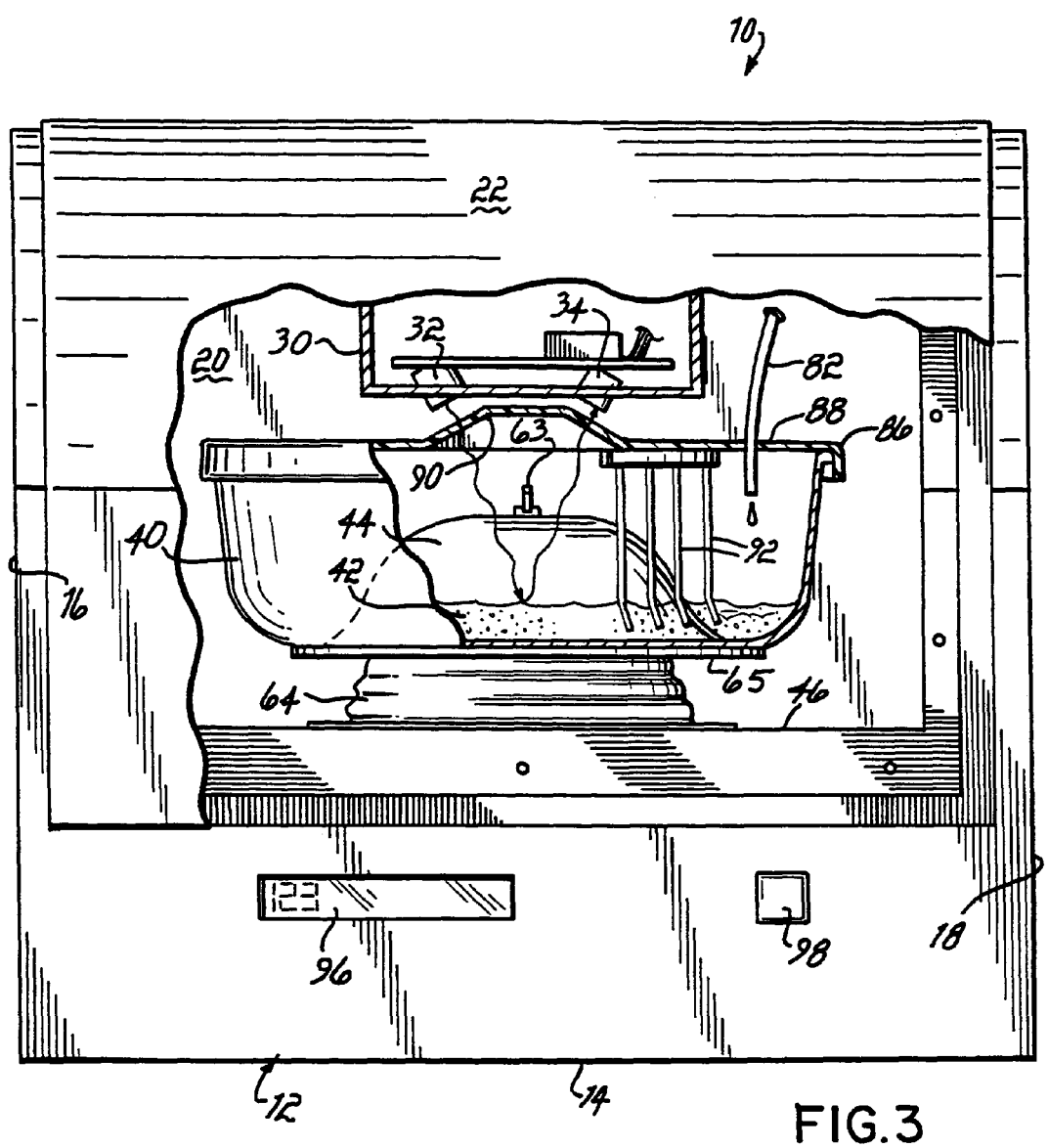
FIG. 3 is a front view of the apparatus, partially broken away.

Referring now to FIGS. 2 and 3, the apparatus 10 is shown in more detail. A support in the form of a bowl 40 is provided for containing a sample 42 of aggregate. The bowl 40 includes an island 44 in the center thereof to direct the aggregate 42 radially outwardly during motion of the bowl 40, which will be described below. A horizontal wall 46 interconnects the front, side and back walls 14, 16, 18 and 20 and provides structure upon which the bowl 40 is mounted.

A motor 48 is mounted to the horizontal wall 46 and includes an output drive shaft 50. Output drive shaft 50 has fixedly secured thereto a plate 52 and an eccentric shaft 54. The axes of rotation of the shafts 50, 54 are angled just off of parallel by approximately 0.75°. The axis of rotation of the shaft 54 is offset from that of shaft 50 a distance d. Preferably, d is approximately 0.078" on average. A bearing 56 encircles eccentric shaft 54. The inner race of the bearing 56 is fixedly secured to the eccentric shaft 54. A counterweight 58 is mounted to the plate 52 to offset or counterbalance the effects of the shaft 54 being offset from the shaft 50 the amount d. The outer race of the bearing 56 is fixedly secured to an inverted flanged cylinder 60. A Z bracket mounts stop a plate 65. A ¼ turn thumb nut 63 removably secures the bowl 40 onto the top of the Z bracket. A rubber boot 64 has an upper end sandwiched between the flanged cylinders 60 and plate 61, and a lower end secured to the horizontal wall 46 via screws 66 or the like. Screws 62 pass through plate Z bracket 61, plate 65, boot 64 and screw into cylinder 60. Boot 64 protects bearing 56, etc. from contamination and also serves to prevent bowl 40 from rotating about its own axis.

Due to the offset d, rotation of motor output shaft 50 causes bowl 40 to move in an "orbital" motion having a radius equal to d. The 0.75° deviation from parallel between the axes of shafts 50, 54 imparts a "wobbling" motion to the bowl 40 and hence sample of aggregate 42.

Referring now to FIGS. 1–3, a water reservoir 80 is mounted to rear wall 20 and includes flexible tubing or a hose 82 connected thereto. Hose 82 preferably has a 0.01 inch diameter nozzle or output end. A pump 84 pumps water from reservoir 80 through hose 82 into bowl 40 at a preferred rate of approximately 8 micro liters per minute. A removable lid 86 seals the sample 42 within the bowl 40, and includes a small hole 88 through which the tube 82 passes. The lid 86 includes a domed region 90. The domed region 90 allows signals from the infrared source 32 and to the infrared detector 34 to pass through the lid 86 normal thereto. Wire fingers 92 are mounted within the bowl 40 and extend downwardly into contact with the sample 42 of aggregate and serve to further break apart particles of the sample 42 by stirring during injection of water into bowl 40. A processor/controller 94 is operably connected to the infrared source 32, infrared detector 34 and to a display panel 96 on front wall 14 of cabinet 12. An on/off switch 98 is also mounted on front wall 14 of cabinet 12.

Figure 4:
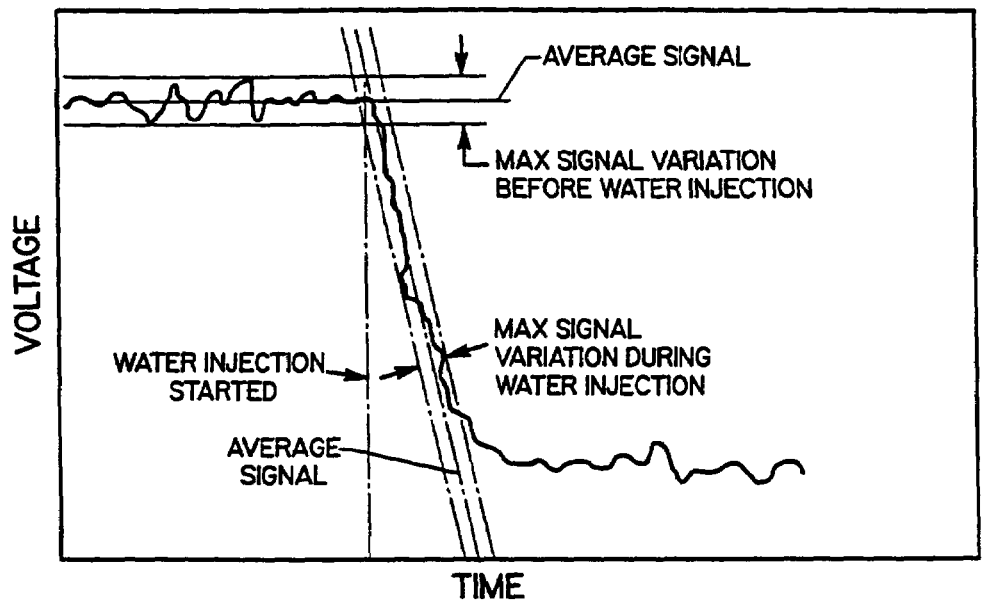
FIG. 4 is a plot of actual voltage of the infrared detector as a function of time as the sample goes from a dry state to an SSD state.
Figure 5:
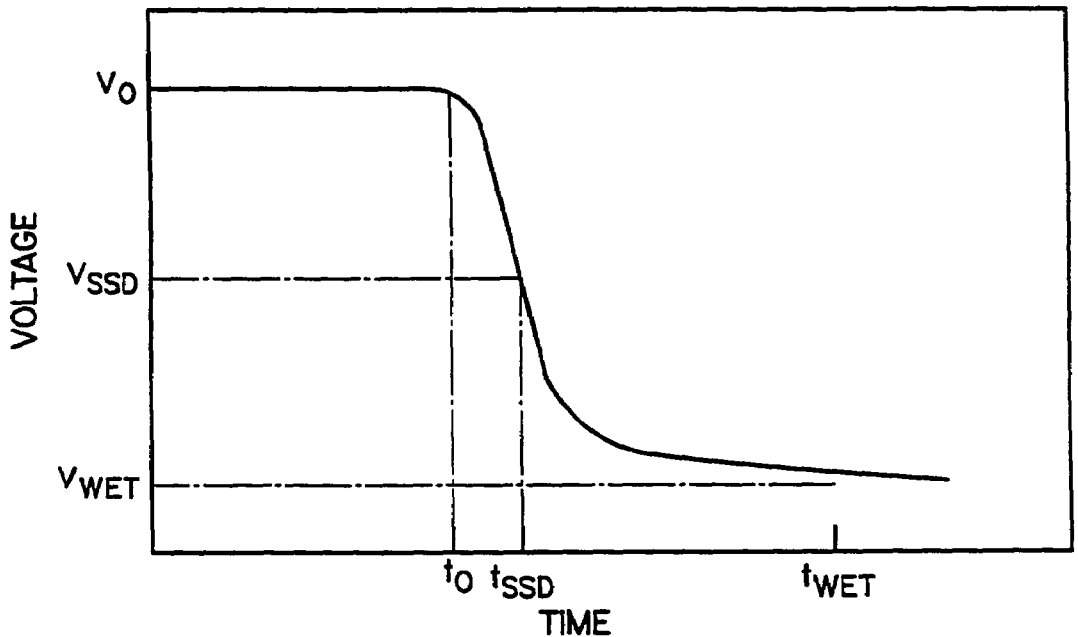
FIG. 5 is an average of the voltage plot of FIG. 4 illustrating the SSD point.

Referring now to FIGS. 4 and 5, the processor/controller 94 preferably processes the reflected infrared signal reflected from the moistened aggregate 42 as a function of time, and controls addition of water to the sample 42 via the pump 84 such that liquid is added to the sample 42 only until the reflected light signal reaches a predetermined value indicative of the sample being at the SSD state, which will be described in more detail below. As is illustrated in FIG. 4, the actual or "raw" infrared reflected voltage indicated by infrared detector 34 as a function of time decreases during addition of water to the sample 42 and during mixing or agitation of the sample 42 therewith. The infrared source 32 and infrared detector 34 are mounted in an isosceles triangle configuration, wherein the IR source and detector define two points and the surface to be measured, i.e. the surface of the aggregate sample 42, defines the third point. Light travels from the infrared source 32 to the aggregate 42, scatters back off the aggregate 42, and then travels to the infrared detector 34. Because water is very optically absorbing at wave lengths above 1.8 micrometers, the signal of the infrared detector 34 will decrease as the voids in the aggregate fill with water. The signal will show a saturating effect when the voids become completely filled with water. At the point where the aggregate 42 becomes wetter than SSD, the slope of the curve shown in FIG. 4 asymptotically approaches zero. The SSD point occurs at a point in time prior thereto, as will be described below in more detail. The processor/controller 94 monitors the infrared reflected signal via an analog to digital converter (not shown). To isolate the reflected infrared signal from any thermal effect noise of the thermopile infrared detector 34, the infrared source 32 is modulated at approximately one Hz. The electrical circuit (not shown) associated with the IR source 32 and detector 34 preferably includes an electronic high pass filter and a signal rectifier to provide a dc output signal for the processor/controller 94.

Referring now specifically to FIG. 5, FIG. 5 illustrates the average of the voltage signal versus time curve of FIG. 4 as averaged by the processor/controller 94. The voltage signal $V_0$ at time $t_0$ is the voltage representative of the IR reflectance of the dry aggregate. The voltage signal $V_{wet}$ at time $t_{wet}$ is the voltage representative of the IR reflectance of the aggregate wetter than SSD. It has been empirically determined that the voltage signal $V_{ssd}$ at time $t_{ssd}$ is approximately equal to the average of $V_0$ and $V_{wet}$. In other words, it has been empirically determined that $V_{ssd}$ is approximately equal to $(V_0+V_{wet})/2$. It has also been determined empirically that $V_{wet}$ for most aggregates is approximately a constant 0.08 Volts. Thus, once $V_0$ has been measured for a particular aggregate, $V_{ssd}$ can be readily calculated with the above formula and the processor/controller can then be programmed with the calculated $V_{ssd}$ value. The processor/controller monitors the voltage and controls addition of water to the sample 42 such that water is added only until the voltage reaches the predetermined $V_{ssd}$ value.

To automatically determine the PA of an aggregate, the apparatus 10 could advantageously incorporate a weighing scale 100 to record the weight of the sample 42 dry and at the SSD point, in real time.

To determine the SSD state of an aggregate going from wet to dry, the apparatus would include a heater 102 controlled by the processor/controller 94 to perform the reverse of the above, i.e. to remove liquid from the sample 42 by heating it.

Cabinet 12 may be fabricated of aluminum sheet. A suitable material from which to fabricate the bowl 40 is polypropylene. The thickness of the polypropylene in the area of the domed region 90 is preferably 0.02 inches or less. A suitable infrared source or emitter 32 is ReflectIR available from Ion Optics of Waltham, Mass. A suitable infrared detector or receiver 34 is DZMHS005 available from Dexter Research of Dexter, Mich. A suitable motor 48 is Type 04 available from Faseo Motors of Ozark, Mo. A suitable pump 84 is 090SP-24-8 available from Bio-Chem Valve, Inc. of Benton, N.J.

Figure 6:
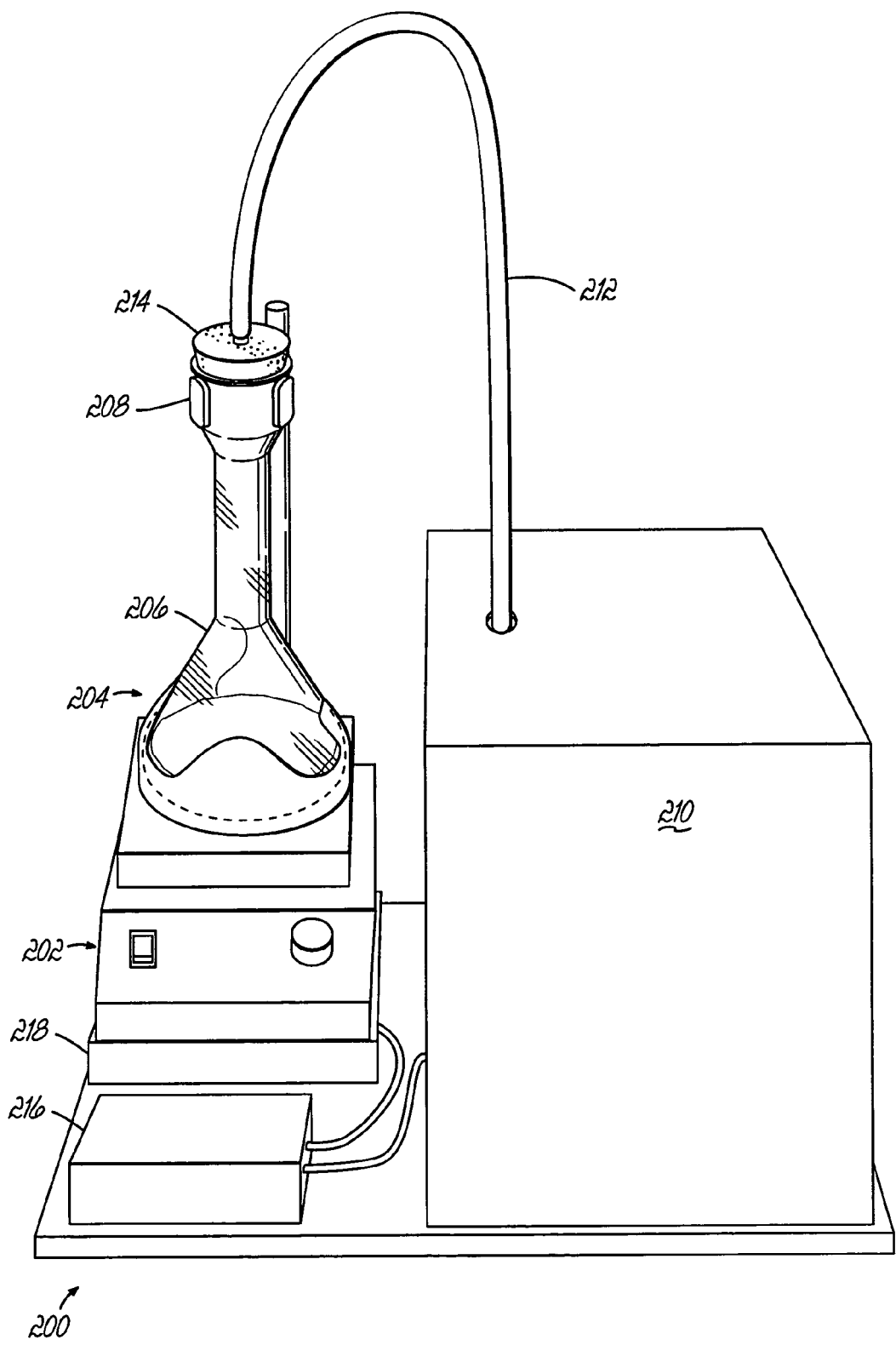
FIG. 6 is a perspective view of an apparatus for determining liquid absorption of an aggregate.

Referring now to FIG. 6 there is illustrated apparatus 200 for determining liquid absorption of a material. The apparatus 200 comprises a shaker apparatus 202 for supporting and agitating a container 204 containing a material specimen 206. Shaker apparatus 202 can be, for example, a Vortex Maxi Mix III, model number M65820-33, available from the assignee. Container 204 can be, for example, a 500 ml volumetric flask. Container 204 can be loosely or hard mounted to a support 208 to prevent vortexing. A vacuum source 210 is connected to the container 204 via hose 212 and stopper 214. A processor/controller 216 is operably associated with the shaker apparatus 202 and the vacuum source 210 and controls operation of the shaker 202 and vacuum 210 in response to inputs received from a technician. The processor/controller 216 preferably controls the vibration frequency, amplitude and duration of the shaker 202 and the vacuum pressure and duration of the vacuum 210. Optionally a weighing device 218 can be included. The processor/controller 216 would also be in operable association with the weighing device 218 such that the processor/controller 216 causes the weighing device 218 to weight the sample 204 and liquid before and after operation of the shaker 202 and vacuum 210. The processor/controller 216 would then determine the difference in the two weights and from the difference compute the liquid absorption and/or apparent specific gravity which would then be displayed on a display.

In use of the apparatus 200, 250 ml of water is poured into the container 204, a sample of material 206 is placed into the container 204 and a period of time is allowed to pass, for example 5 minutes. Then, additional water is added up to a calibration mark on the container 204. The container 204, sample 206 and water are then weighed and the initial weight is recorded. The container 204 and its contents are then subjected to a series of agitation and vacuum steps. After the series of agitation and vacuum steps water is again added up to the calibration mark. The container 204, sample 206 and water are again weighed and the final weight is recorded. The difference in the initial and final weights is directly related to the liquid absorption of the sample 206. By dividing the difference by the dry weight of the sample, and by multiplying the quotient by a constant, about 0.5, and by 100, the percent liquid absorption is obtained. The initial and final weights can also be used to calculate apparent specific gravity, and a film coefficient, the latter being a parameter which relates to the $V_{ssd}$, one of the parameters disclosed in the assignee's own U.S. Pat. No. 6,486,475. By adding the dry sample weight to the weight of the container, sample and liquid with the liquid at the calibration mark on the container, subtracting from that sum the final weight, and dividing that difference into the dry sample weight, one can determine the apparent specific gravity of the aggregate.

The agitation and vacuum steps can be performed simultaneously or sequentially. Preferably the agitation step is performed first and the vacuum step is performed second. Several agitation steps can be alternated with several vacuum steps. The length of the agitation and vacuum steps is preferably about 3 to 5 minutes. A vacuum of from about 22 inches of Hg to about 28 inches of Hg is preferred. One particular routine is to perform agitation for about 3 minutes, perform agitation and apply a vacuum of about 22 inches of Hg for about 3 minutes, and perform agitation and apply a vacuum of about 28 inches of Hg for about 5 minutes. Such a routine can be selected as inputs to the processor/controller 216 which then controls the magnitude and duration of the vibration of the shaker 202 and of the pressure of the vacuum 210.

The invention thus permits a technician to determine a material's liquid absorption, percent liquid absorption, apparent specific gravity and film coefficient in about ten to twenty minutes, as apposed to about twelve hours for the current manual hand method.

Those skilled in the art will readily recognize numerous adaptations and modifications which can be made to the present invention which will result in an improved method and apparatus for determining liquid absorption of aggregate, yet all of which will fall within the spirit and scope of the present invention as defined in the following claims. For example, while the invention has been described in connection with determining the SSD state of an aggregate in going from a dry condition of the aggregate to a wet condition, the invention can also be practiced in the reverse, i.e. going from an overly saturated condition of the aggregate to a SSD condition of the aggregate. However, the SSD state of the aggregate, as determined by infrared reflection, is more readily obtained for the dry to wet process than for the wet to dry process. Additionally, the wet to dry process requires a heating means be incorporated into the apparatus. Accordingly, the invention is to be limited only by the scope of the following claims and their equivalents.

What is claimed is:

1. A method of determining liquid absorption of an aggregate, the method comprising:
   providing a shaker apparatus, a vacuum source and a container;
   placing a sample of the aggregate in the container;
   adding liquid to the container sufficient to reach a calibration mark on the container;
   weighing the sample and liquid;
   mounting the container to the shaker apparatus;
   connecting the vacuum source to the container;
   agitating the sample and liquid with the shaker apparatus;
   applying a vacuum to the sample and liquid with the vacuum source;
   after the agitation and vacuum steps, adding liquid to the container sufficient to again reach the calibration mark on the container;
   again weighing the sample and liquid; and
   subtracting the initial weight of the sample and liquid from the final weight of the sample and liquid in order to determine the liquid absorption of the aggregate.

2. The method of claim 1 further comprising the steps of:
   dividing the difference between the initial and final weights of the sample and liquid by the dry weight of the sample; and
   multiplying the quotient by a constant and by 100 to determine the percent liquid absorption of the aggregate.

3. The method of claim 2 wherein the constant is about 0.5.

4. The method of claim 1 wherein the agitation and vacuum steps are performed simultaneously.

5. The method of claim 1 wherein the agitation and vacuum steps are performed sequentially.

6. The method of claim 1 wherein the agitation step is performed first and the vacuum step is performed second.

7. The method of claim 1 wherein a series of agitation steps are alternated with a series of vacuum steps.

8. The method of claim 1 wherein the agitation step is performed for about 5 minutes and then the vacuum step is performed for 5 about minutes.

9. The method of claim 6 wherein the vacuum step applies a vacuum of about 22 inches of Hg.

10. The method of claim 6 where the vacuum step applies an initial vacuum of about 22 inches of Hg and a final vacuum of about 28 inches of Hg.

11. The method of claim 1 wherein agitation is performed for about 3 minutes, agitation and about 22 inches Hg vacuum is performed for about 3 minutes and agitation and about 28 inches Hg vacuum is performed for about 5 minutes.

12. The method of claim 1 further comprising the steps of:
   adding the dry sample weight to the weight of the container, sample and liquid with the liquid at the calibration mark on the container;
   subtracting from that sum the final weight; and
   dividing that difference into the dry sample weight to determine the apparent specific gravity of the aggregate.

* * * * *

UNITED STATES PATENT AND TRADEMARK OFFICE
CERTIFICATE OF CORRECTION

PATENT NO. : 6,986,279 B2  Page 1 of 2
APPLICATION NO. : 10/667172
DATED : January 17, 2006
INVENTOR(S) : Lockwood et al.

It is certified that error appears in the above-identified patent and that said Letters Patent is hereby corrected as shown below:

In column 2, line 12, change "from technician testing the aggregate to the next." to --from one technician testing the aggregate to the next.--.

In column 2, line 41, change "Dust can also adversely effect mechanical parts" to --Dust can also adversely affect mechanical parts--.

In column 2, line 57, change "dry aggregate to the weight of weight" to --dry aggregate to the weight of water--.

In column 3, line 49, change "0.08 Volts for all aggregate." to --0.08 Volt for all aggregate.--.

In column 4, line 15, change "preferably concludes a lid thereon." to --preferably includes a lid thereon.--.

In column 4, line 37, change "0.08 Volts for all aggregate." to --0.08 Volt for all aggregate.--.

In column 4, line 56, change "initially dry sample is begun to be agitated" to --initially dry sample begins to be agitated--.

In column 5, line 12, change "The constant is preferably about 0.5." to --The constant is preferably about 0.5;--.

In column 5, line 25, change "performed for 5 about minutes." to --performed for about 5 minutes.--.

In column 5, line 25, change "Preferably the vacuum step preferably applies" to --Preferably the vacuum step applies--.

In column 5, line 34, change "comprising a shaker apparatus" to --comprises a shaker apparatus--.

In column 5, line 46, change "The apparatus can further comprising" to --The apparatus can further comprise--.

Signed and Sealed this

Twenty-second Day of June, 2010

David J. Kappos
*Director of the United States Patent and Trademark Office*

In column 6, line 47, change "A Z bracket mounts stop a plate 65." to --A Z bracket mounts atop a plate 65.--.

In column 7, line 61, change "0.08 Volts." to --0.08 Volt.--.

In column 8, line 13, change "preferably 0.02 inches or less." to --preferably 0.02 inch or less.--.

In column 8, line 41, change "to weight the sample" to --to weigh the sample--.

In column 9, line 24, change "as apposed to about twelve hours" to --as opposed to about twelve hours--.

In claim 8, column 10, line 33, change "for 5 about minutes." to --for about 5 minutes.--.

In claim 10, column 10, line 36, change "The method of claim 6 where" to --The method of claim 6 wherein--.